(12) United States Patent
Lipiecki et al.

(10) Patent No.: US 9,410,217 B2
(45) Date of Patent: Aug. 9, 2016

(54) METHOD OF REDUCING A FERMENTATION AND/OR ENZYME INHIBITOR IN A SACCHARIDE-CONTAINING COMPOSITION

(71) Applicant: Renmatix, Inc., King of Prussia, PA (US)

(72) Inventors: Francis Lipiecki, Haddonfield, NJ (US); Sachin Arora, Bryn Mawr, PA (US)

(73) Assignee: Renmatix, Inc., King of Prussia, PA (US)

( * ) Notice: Subject to any disclaimer, the term of this patent is extended or adjusted under 35 U.S.C. 154(b) by 24 days.

(21) Appl. No.: 14/182,565

(22) Filed: Feb. 18, 2014

(65) Prior Publication Data

US 2015/0232958 A1 Aug. 20, 2015

(51) Int. Cl.
C12P 7/06 (2006.01)
C13K 13/00 (2006.01)
C13K 1/04 (2006.01)
C12P 7/10 (2006.01)

(52) U.S. Cl.
CPC ... C13K 1/04 (2013.01); C12P 7/06 (2013.01); C12P 7/10 (2013.01); C13K 13/002 (2013.01); C12P 2203/00 (2013.01); Y02E 50/16 (2013.01); Y02E 50/17 (2013.01)

(58) Field of Classification Search
None
See application file for complete search history.

(56) References Cited

U.S. PATENT DOCUMENTS

| | | | |
|---|---|---|---|
| 5,208,370 A | 5/1993 | Bauer, Jr. et al. | |
| 6,274,212 B1* | 8/2001 | Rule et al. | 428/36.92 |
| 2002/0142410 A1* | 10/2002 | Rangel-Aldao | C12C 5/02 435/161 |
| 2011/0008826 A1* | 1/2011 | Hanakawa et al. | 435/41 |

FOREIGN PATENT DOCUMENTS

| | | |
|---|---|---|
| WO | WO 2011/080129 A2 | 7/2011 |
| WO | WO 2011/080130 A2 | 7/2011 |
| WO | WO 2013/122903 A1 | 8/2013 |

OTHER PUBLICATIONS

Lichtenthaler, Green Chemistry, 2001, 3, 201-209.*
Layer, Amines, Aromatic Phenylenediamines, Amines, Aromatic, Kirk-Othmer Encyclopedia of Chemical Technology, Dec. 4, 2000.*
Larsen, Solid-Supported Reagents for Organic Synthesis, MacMillion Group Meeting, Dec. 6, 2001.*
Cavka et al., "Detoxification of lignocellulosic hydrolysates using sodium borohydride," *Bioresource Technology* 136, 368-376 (2013).
Jönsson et al., "Bioconversion of lignocelluloses: inhibitors and detoxification," *Biotechnology for Biofuels*, 6:16, 1-10 (2013).
Larsson et al., "Comparison of Different Methods for the Detoxification of Lignocellulose Hydrolyzates of Spruce," *Applied Biochemistry and Biotechnology*, 77-79, 91-103 (1999).
Palmqvist et al., "Fermentation of lignocellulosic hydrolysates. I: inhibition and detoxification," Bioresource Technology 74, 17-24 (2000).
Palmqvist et al., "Fermentation of lignocellulosic hydrolysates. II: inhibitors and mechanisms of inhibition," Bioresource Technology 74, 25-33 (2000).

* cited by examiner

*Primary Examiner* — Layla Berry
(74) *Attorney, Agent, or Firm* — Travis B Gasa; Andrew G Bunn; Kristen J Harrell

(57) ABSTRACT

Provided is a method of treating a saccharide-containing composition, the method comprising contacting a composition containing a saccharide with a compound of formula (I) or a salt thereof

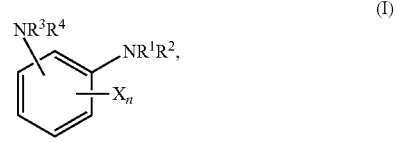

(I)

wherein $R^1$-$R^4$, X, and n are as described herein. Further provided is a composition comprising a saccharide and a compound of formula (I) or a salt thereof.

26 Claims, No Drawings

METHOD OF REDUCING A FERMENTATION AND/OR ENZYME INHIBITOR IN A SACCHARIDE-CONTAINING COMPOSITION

BACKGROUND OF THE INVENTION

Lignocellulosic feedstocks comprise mainly of cellulose, hemicelluloses, and lignin. Lignocellulosic feedstocks typically are obtained from renewable resources, such as agriculture, forests, and refineries associated therewith and are not considered to be food sources. In view of these aspects, lignocellulosic feedstocks are considered desirable for the production of biofuels, chemicals, and polymers. In particular, biofuels, such as ethanol and butanol, typically are produced from a lignocellulosic feedstock through a fermentation process. However, given the complex makeup of a lignocellulosic feedstock and the many processes employed to hydrolyze the feedstock, the issue of fermentation inhibitors becomes a problem.

During the hydrolysis of a lignocellulosic feedstock various compounds are formed that can inhibit fermentation and/or enzymatic processes. One class of known fermentation inhibitors is aldehyde compounds, such as furfural and hydroxymethylfurfural (HMF). Such aldehyde compounds can inhibit the fermentation process if not removed from or reduced in concentration in the mixture. A process called overliming is known to reduce concentration of aldehydes and other fermentation and/or enzyme inhibitors in a saccharide-containing composition. In such a process, calcium oxide (i.e., lime) is added to a crude saccharide-containing composition thereby elevating the pH, and elevated temperatures and forceful mixing typically are employed. The composition typically is returned to about neutral pH, and solid gypsum produced as a by-product must be filtered out of the mixture. While an overliming method typically reduces the overall concentration of aldehyde compounds and other fermentation and/or enzyme inhibitors, the process is tedious and typically results in sugar degradation.

Thus, there continues to be a need for providing an improved method of reducing the concentration of fermentation and/or enzyme inhibitors in a saccharide-containing composition, e.g., a composition derived from a lignocellulosic feedstock.

It will be appreciated that this background description has been created by the inventors to aid the reader and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims and not by the ability of any disclosed feature to solve any specific problem noted herein.

BRIEF SUMMARY OF THE INVENTION

In one aspect, the invention provides a method of treating a saccharide-containing composition comprising, consisting of, or consisting essentially of contacting a composition containing a saccharide with a compound of formula (I) or a salt thereof

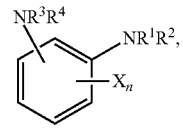

(I)

wherein $R^1$-$R^4$, X, and n are as described herein.

In another aspect, the invention provides a composition comprising, consisting of, or consisting essentially of a saccharide and a compound of formula (I) or a salt thereof

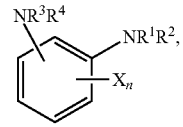

(I)

wherein $R^1$-$R^4$, X, and n are as described herein.

When a compound of formula (I) contacts a saccharide-containing composition, the concentration of one or more fermentation inhibitors contained therein is reduced, typically to a non-inhibitory level, e.g., a level that does not inhibit fermentation of, and/or enzymatic processes on, the saccharide-containing composition. As a result, the fermentation of, and/or enzymatic process on, the saccharide-containing composition is improved, and the overall yield of a product, such as ethanol and/or butanol, is increased from the saccharide-containing composition.

DETAILED DESCRIPTION OF THE INVENTION

The invention provides a method of treating a saccharide-containing composition comprising contacting a composition containing a saccharide with a compound of formula (I) or a salt thereof

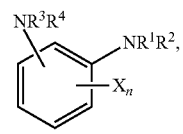

(I)

wherein
(1) $R^1$-$R^4$ are the same or different and each is independently selected from —H, -M, $C_1$-$C_8$ alkyl, $C_2$-$C_8$ alkenyl, $C_3$-$C_6$ cycloalkyl, aryl, heteroaryl, alkylene oxide, oligoalkylene oxide, polyalkylene oxide, —$R^7OR^8$, —$R^7OM$, —$CONH_2$, —$R^7CONH_2$, —CONHOH, —$R^7CONHOH$, —$C(O)OR^7$, —$R^8C(O)OR^7$, —C(O)OM, —$R^7C(O)OM$, —$C(O)R^7$, —$R^8C(O)R^7$, —$C(O)N(R^7)R^8$, —$R^9C(O)N(R^7)R^8$, —$C(O)NR^7SO_2N(R^8)R^9$, —$R^{10}C(O)NR^7SO_2N(R^8)R^9$, —$R^7PO_4$, —$R^7PO(OH)_2$, —$R^7PO(OH)(OR^8)$, —$R^7PO(OR^8)_2$, —$R^7SO_3H$, —$R^7SO_2NR^8OH$, —$R^7SR^8$, —$R^7SOR^8$, —$R^7SO_2R^8$, —$R^7SO_2NR^8(R^9)$, —$R^7SO_2NR^8CON(R^9)R^{10}$, —$R^7NO_2$, —$R^7NR^8R^9$, —$R^7NR^8C(O)R^9$, —$R^7N(R^8)C(O)R^9$, —$R^7NR^8SO_2R^9$, —$R^7N(R^8)SO_2R^9$, —$R^7NR^8R^9R^{10}M$, —$R^7R^8M$, and any of the foregoing groups other than —H that is optionally substituted; or
any two of $R^1$-$R^4$ taken together is a divalent counterion, and the other two of $R^1$-$R^4$ is defined as in (1); or any three of $R^1$-$R^4$ taken together is a trivalent counterion, and the other one of $R^1$-$R^4$ is defined as in (1); or any two of $R^1$-$R^4$ taken together is a divalent counterion, and the other two of $R^1$-$R^4$ is the same or a different divalent counterion; or all of $R^1$-$R^4$ taken together is a tetravalent counterion;

(2) each X is the same or different and each is independently selected from —H, —OH, $C_1$-$C_8$ alkyl, $C_2$-$C_8$ alkenyl, $C_3$-$C_6$ cycloalkyl, aryl, heteroaryl, alkylene oxide, oligoalkylene oxide, polyalkylene oxide, heterocycloalkyl, $C_1$-$C_8$ haloalkyl, halo, —CN, —$R^7$CN, —$NO_2$, —$R^7NO_2$, —$OR^7$, —$R^7OR^8$, —$OR^7OR^8$, —OM, —$R^7OM$, —$CONH_2$, —$R^7CONH_2$, —CONHOH, —$R^7CONHOH$, —$C(O)OR^7$, —$R^8C(O)OR^7$, —C(O)OM, —$R^7C(O)OM$, —$C(O)R^7$, —$R^8C(O)R^7$, —$C(O)N(R^7)R^8$, —$R^9C(O)N(R^7)R^8$, —$C(O)NR^7SO_2N(R^8)R^9$, —$R^{10}C(O)NR^7SO_2N(R^8)R^9$, —$PO_4$, —$R^7PO_4$, —$PO(OH)_2$, —$R^7PO(OH)_2$, —$PO(OH)(OR^7)$, —$R^8PO(OH)(OR^7)$, —$PO(OR^7)_2$, —$R^8PO(OR^7)_2$, —$SO_3H$, —$SO_3M$, —$R^7SO_3H$, —$R^7SO_3M$, —$R^7SO_3R^8$, —$SO_2NR^7OH$, —$R^8SO_2NR^7OH$, —$SR^7$, —$R^8SR^7$, —$SOR^7$, —$R^8SOR^7$, —$SO_2R^7$, —$R^8SO_2R^7$, —$SO_2NR^7(R^8)$, —$R^9SO_2NR^7(R^8)$, —$SO_2NR^7CON(R^8)R^9$, —$R^{10}SO_2NR^7CON(R^8)R^9$, —$NR^7R^8$, —$R^9NR^7R^8$, —$NR^7C(O)R^8$, —$R^9NR^7C(O)R^8$, —$N(R^7)C(O)R^8$, —$R^9N(R^7)C(O)R^8$, —$NR^7SO_2R^8$, —$R^9NR^7SO_2R^8$, —$N(R^7)SO_2R^8$, —$R^9N(R^7)SO_2R^8$, —$NR^7R^8R^9M$, —$R^{10}NR^7R^8R^9M$, and any of the foregoing groups other than —H that is optionally substituted; or two X substituents can be taken together with the carbon atoms to which they are attached to form a 5- or 6-membered aryl, cycloalkyl or heterocycloalkyl comprising 1 or 2 heteroatoms selected from the group consisting of N, O, and S; and (3) $R^7$, $R^8$, $R^9$, and $R^{10}$ are the same or different and each is independently selected from —H, $C_1$-$C_8$ alkyl, $C_3$-$C_6$ cycloalkyl, aryl, heteroaryl, alkylene oxide, oligoalkylene oxide, polyalkylene oxide, and any of the foregoing groups other than —H that is optionally substituted; and (4) M is a monovalent counterion; and (5) n is 0 or an integer of 1 to 4.

The invention further provides a composition comprising a saccharide and a compound of formula (I) or a salt thereof

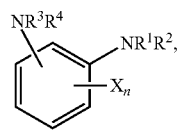

(I)

wherein (1) $R^1$-$R^4$ are the same or different and each is independently selected from —H, -M, $C_1$-$C_8$ alkyl, $C_2$-$C_8$ alkenyl, $C_3$-$C_6$ cycloalkyl, aryl, heteroaryl, alkylene oxide, oligoalkylene oxide, polyalkylene oxide, —$R^7OR^8$, —$R^7OM$, —$CONH_2$, —$R^7CONH_2$, —CONHOH, —$R^7CONHOH$, —$C(O)OR^7$, —$R^8C(O)OR^7$, —C(O)OM, —$R^7C(O)OM$, —$C(O)R^7$, —$R^8C(O)R^7$, —$C(O)N(R^7)R^8$, —$R^9C(O)N(R^7)R^8$, —$C(O)NR^7SO_2N(R^8)R^9$, —$R^{10}C(O)NR^7SO_2N(R^8)R^9$, —$R^7PO_4$, —$R^7PO(OH)_2$, —$R^7PO(OH)(OR^8)$, —$R^7PO(OR^8)_2$, —$R^7SO_3H$, —$R^7SO_2NR^8OH$, —$R^7SR^8$, —$R^7SOR^8$, —$R^7SO_2R^8$, —$R^7SO_2NR^8(R^9)$, —$R^7SO_2NR^8CON(R^9)R^{10}$, —$R^7NO_2$, —$R^7NR^8R^9$, —$R^7NR^8C(O)R^9$, —$R^7N(R^8)C(O)R^9$, —$R^7NR^8SO_2R^9$, —$R^7N(R^8)SO_2R^9$, —$R^7NR^8R^9R^{10}M$, —$R^7R^8M$, and any of the foregoing groups other than —H that is optionally substituted; or any two of $R^1$-$R^4$ taken together is a divalent counterion, and the other two of $R^1$-$R^4$ is defined as in (1); or any three of $R^1$-$R^4$ taken together is a trivalent counterion, and the other one of $R^1$-$R^4$ is defined as in (1); or any two of $R^1$-$R^4$ taken together is a divalent counterion, and the other two of $R^1$-$R^4$ is the same or a different divalent counterion; or all of $R^1$-$R^4$ taken together is a tetravalent counterion;

(2) each X is the same or different and each is independently selected from —H, —OH, $C_1$-$C_8$ alkyl, $C_2$-$C_8$ alkenyl, $C_3$-$C_6$ cycloalkyl, aryl, heteroaryl, alkylene oxide, oligoalkylene oxide, polyalkylene oxide, heterocycloalkyl, $C_1$-$C_8$ haloalkyl, halo, —CN, —$R^7$CN, —$NO_2$, —$R^7NO_2$, —$OR^7$, —$R^7OR^8$, —$OR^7OR^8$, —OM, —$R^7OM$, —$CONH_2$, —$R^7CONH_2$, —CONHOH, —$R^7CONHOH$, —$C(O)OR^7$, —$R^8C(O)OR^7$, —C(O)OM, —$R^7C(O)OM$, —$C(O)R^7$, —$R^8C(O)R^7$, —$C(O)N(R^7)R^8$, —$R^9C(O)N(R^7)R^8$, —$C(O)NR^7SO_2N(R^8)R^9$, —$R^{10}C(O)NR^7SO_2N(R^8)R^9$, —$PO_4$, —$R^7PO_4$, —$PO(OH)_2$, —$R^7PO(OH)_2$, —$PO(OH)(OR^7)$, —$R^8PO(OH)(OR^7)$, —$PO(OR^7)_2$, —$R^8PO(OR^7)_2$, —$SO_3H$, —$SO_3M$, —$R^7SO_3H$, —$R^7SO_3M$, —$R^7SO_3R^8$, —$SO_2NR^7OH$, —$R^8SO_2NR^7OH$, —$SR^7$, —$R^8SR^7$, —$SOR^7$, —$R^8SOR^7$, —$SO_2R^7$, —$R^8SO_2R^7$, —$SO_2NR^7(R^8)$, —$R^9SO_2NR^7(R^8)$, —$SO_2NR^7CON(R^8)R^9$, —$R^{10}SO_2NR^7CON(R^8)R^9$, —$NR^7R^8$, —$R^9NR^7R^8$, —$NR^7C(O)R^8$, —$R^9NR^7C(O)R^8$, —$N(R^7)C(O)R^8$, —$R^9N(R^7)C(O)R^8$, —$NR^7SO_2R^8$, —$R^9NR^7SO_2R^8$, —$N(R^7)SO_2R^8$, —$R^9N(R^7)SO_2R^8$, —$NR^7R^8R^9M$, —$R^{10}NR^7R^8R^9M$, and any of the foregoing groups other than —H that is optionally substituted; or two X substituents can be taken together with the carbon atoms to which they are attached to form a 5- or 6-membered aryl, cycloalkyl or heterocycloalkyl comprising 1 or 2 heteroatoms selected from the group consisting of N, O, and S; and (3) $R^7$, $R^8$, $R^9$, and $R^{10}$ are the same or different and each is independently selected from —H, $C_1$-$C_8$ alkyl, $C_3$-$C_6$ cycloalkyl, aryl, heteroaryl, alkylene oxide, oligoalkylene oxide, polyalkylene oxide, and any of the foregoing groups other than —H that is optionally substituted; and (4) M is a monovalent counterion; and (5) n is 0 or an integer of 1 to 4.

The saccharide is any suitable sugar and typically includes at least one five- or six-carbon sugar (e.g., pentose and hexose sugar residues and combinations thereof). Examples of pentose sugars include arabinose, lyxose, ribose, xylose, ribulose, and xylulose. Examples of hexose sugars include allose, altrose, glucose, mannose, gulose, idose, galactose, talose, psicose, fructose, sorbose, and tagatose. In some aspects, the composition comprises xylose (e.g., D-xylose and/or L-xylose), arabinose (e.g., D-arabinose and/or L-arabinose), mannose (e.g., D-mannose and/or L-mannose), glucose (e.g., D-glucose and/or L-glucose), galactose (e.g., D-galactose and/or L-galactose), or a combination thereof. In certain embodiments, the saccharide is selected from a monosaccharide that is xylose, a monosaccharide that is glucose, an oligosaccharide comprising xylose (e.g., xylose monomeric units), an oligosaccharide comprising glucose (e.g., glucose monomeric units), a polysaccharide comprising xylose (e.g., xylose monomeric units), a polysaccharide comprising glucose (e.g., glucose monomeric units), and any combination thereof. In certain embodiments, the saccharide is xylose and/or glucose.

In certain aspects, the composition further comprises a fermentation inhibitor and/or an enzyme inhibitor. The fermentation inhibitor can be any compound or combination of compounds that inhibit(s) fermentation, and the enzyme inhibitor can be any compound or combination of compounds that inhibit(s) enzyme function. In some aspects, the fermentation inhibitor and/or enzyme inhibitor is selected from an aldehyde compound, an aromatic compound (e.g., a phenolic compound), a benzoquinone compound, an acid, or any combination thereof. In certain aspects, the composition will further comprise an aldehyde compound. An aldehyde compound is any compound comprising at least one —C(O)H moiety. Typically the aldehyde will form from the dehydration of sugar moieties, such as C5 saccharides and C6 saccharides, particularly those described herein, and/or the aldehyde will form from the depolymerization (e.g., breakdown) of lignin. The aldehyde can be at least one aldehyde selected, for example, from hydroxymethylfurfural (HMF), furfural, syringaldehyde, homosyringaldehyde, coniferaldehyde, benzaldehyde, substituted benzaldehyde (e.g., p-hydroxybenzaldehyde, 3,4-dihydroxybenzaldehyde, 3,4,5-trihydroxybenzaldehyde, etc.), vanillin, homovanillin, 4-hydroxy-3-methoxy-cinnamaldehyde, sinapaldehyde, and acetaldehyde. In some compositions, mixtures of these aldehydes will be present. In some embodiments, the aldehyde is HMF and/or syringaldehyde.

The inventive method typically will comprise reducing the amount of any fermentation inhibitor and/or enzyme inhibitor in the composition after the composition has been contacted with the compound of formula (I). The term "reducing" means that the concentration of at least one fermentation inhibitor and/or enzyme inhibitor (e.g., aldehyde compound) in the composition after contacting the composition with the compound of formula (I) is lower than the concentration for the same fermentation inhibitor and/or enzyme inhibitor (e.g., same aldehyde compound) before the composition has been contacted with the compound of formula (I). The level of reduction can be any amount, including a concentration that is below the detection limit for a given means of analysis. For example, the level of reduction in the amount of a particular fermentation inhibitor and/or enzyme inhibitor (e.g., aldehyde compound) can be any level, including a reduction of 100% (e.g., a reduction of at least about 99%, at least about 98%, at least about 97%, at least about 96%, at least about 95%, at least about 94%, at least about 93%, at least about 92%, at least about 91%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, or at least about 10%). The concentration of fermentation inhibitor (e.g., aldehyde compound) can be measured by any suitable method, e.g., gas chromatography-mass spectrometry (GC-MS), liquid chromatography-mass spectrometry (LC-MS), high performance liquid chromatography (HPLC), including HPLC with a refractive index detector, spectrophotometry using, for example, the Prussian blue method or Folin-Ciocalteu's reagent, or a biosensor.

In a preferred embodiment, the concentration of fermentation inhibitor and/or enzyme inhibitor in the composition is reduced after contacting the composition with the compound of formula (I) to a level that does not inhibit or interfere with one or more, preferably any, subsequent processing steps (e.g., fermentation, distillation, enzymatic treatment, etc.). In certain aspects, if the enzyme inhibitor and/or fermentation inhibitor (e.g., aldehyde compound) concentration of the composition prior to contacting the composition with the compound of formula (I) is greater than about 1.5 g/L (e.g., about 2 g/L or more, about 2.5 g/L or more, about 3 g/L or more, about 3.5 g/L or more, about 4 g/L or more, about 5 g/L or more, about 6 g/L or more, about 7 g/L or more, or about 8 g/L or more), then the fermentation inhibitor and/or enzyme inhibitor (e.g., aldehyde compound) concentration in the composition is reduced to about 1.5 g/L or less (e.g., about 1.25 g/L or less, about 1 g/L or less, about 0.9 g/L or less, about 0.8 g/L or less, about 0.7 g/L or less, about 0.6 g/L or less, about 0.5 g/L or less, about 0.4 g/L or less, about 0.3 g/L or less, about 0.2 g/L or less, or about 0.1 g/L or less) after contacting the composition with the compound of formula (I). In some embodiments, the lower limit for any or all of the aforementioned ranges is greater than 0 g/L (i.e., exclusive of 0 g/L). In other embodiments, the lower limit for any or all of the aforementioned ranges is 0 g/L (i.e., inclusive of 0 g/L). In some embodiments, after contacting the composition with the compound of formula (I), the enzyme inhibitor or fermentation inhibitor (e.g., aldehyde compound) concentration in the composition is reduced to an undetectable level (e.g., about 0 g/L).

The compound of formula (I) of the invention can be present in the composition in any suitable concentration. Typically, the concentration will be an amount effective to provide a desired result, e.g., to reduce the concentration of at least one enzyme inhibitor and/or fermentation inhibitor. Suitable ways to express concentrations of the compound of formula (I) include (a) parts by weight of the compound of formula (I) relative to parts by volume of the saccharide-containing composition, (b) grams of the compound of formula (I) relative to about 100 g of the saccharide-containing composition, (c) grams of the compound of formula (I) relative to about 200 ppm of one or more fermentation and/or enzyme inhibitors present in the saccharide-containing composition, and/or (d) grams of the compound of formula (I) relative to about 200 g of one or more monosaccharides present in 1 L of the saccharide-containing composition. The amounts "about 100 g of the saccharide-containing composition," "about 200 ppm of one or more fermentation and/or enzyme inhibitors," and "about 200 g of one or more monosaccharides present in 1 L of the saccharide-containing composition" do not limit the mass of saccharide-containing composition, amount of fermentation and/or enzyme inhibitors, or the amount of one or more monosaccharides present in 1 L of the saccharide-containing composition, respectively. Rather, these expressions merely represent convenient units of measure for facilitating relative comparisons to convey suitable amounts of the compound of formula (I).

Suitable concentrations of the compound of formula (I) include at least 0.001 part by weight compound of formula (I) relative to 1 part by volume of composition (e.g., at least 0.002 part, at least 0.005 part, at least 0.01 part, at least 0.015 part, at least 0.02 part, at least 0.025 part, at least 0.03 part, at least 0.04 part, at least 0.05 part, at least 0.06 part, at least 0.08 part, at least 0.1 part, at least 0.2 part, at least 0.3 part, at least 0.4 part, at least 0.5 part, at least 0.6 part, at least 0.8 part, or at least 1 part by weight compound of formula (I) relative to 1 part by volume of composition). The maximum amount of the compound of formula (I) is not particularly limited, but typically will be about 10 parts or less by weight compound of formula (I) relative to 1 part by volume of composition (e.g., about 9 parts or less, about 8 parts or less, about 7 parts or less, about 6 parts or less, about 5 parts or less, about 4 parts or less, about 3 parts or less, about 2 parts or less, about 1 part or less, or about 0.5 part or less by weight compound of formula (I) relative to 1 part by volume of composition). These lower and upper limits with respect to the amount of compound of formula (I) can be used in any combination to describe the concentration range of the compound of formula (I). The weight units and volume units can be any pairing of mg, g, and kg (weights) and mL and L (volumes). Typically, the concentration of the compound of formula (I) is expressed in g/mL. In a preferred embodiment, the amount of compound of formula (I) is about 0.002 g to about 0.03 g (more preferably about 0.005 g to about 0.02 g), per mL of saccharide-containing composition.

Suitable amounts of the compound of formula (I) relative to 100 g of the saccharide-containing composition can be about 0.01 g or more, e.g., about 0.02 g or more, about 0.04 g or more, about 0.06 g or more, about 0.08 g or more, about 0.1 g or more, about 0.2 g or more, about 0.3 g or more, about 0.4 g or more, about 0.5 g or more, about 0.6 g or more, about 0.7 g or more, about 0.8 g or more, about 0.9 g or more, about 1 g or more, about 1.1 g or more, about 1.2 g or more, about 1.3 g or more, about 1.4 g or more, about 1.5 g or more, about 1.6 g or more, about 1.7 g or more, about 1.8 g or more, about 1.9 g or more, about 2 g or more, about 2.2 g or more, about 2.4 g or more, about 2.6 g or more, about 2.8 g or more, about 3 g or more, about 3.5 g or more, about 4 g or more, about 4.5 g or more, about 5 g or more, about 5.5 g or more, about 6 g or more, about 6.5 g or more, about 7 g or more, about 7.5 g or more, about 8 g or more, about 8.5 g or more, about 9 g or more, about 9.5 g or more, about 10 g or more, about 15 g or more, or about 20 g or more. The maximum amount of compound of formula (I) is not particularly limited but typically will be about 25 g or less, e.g., about 20 g or less, about 15 g or less, about 10 g or less, about 9.5 g or less, about 9 g or less, about 8.5 g or less, about 8 g or less, about 7.5 g or less, about 7 g or less, about 6.5 g or less, about 6 g or less, about 5.5 g or less, about 5 g or less, about 4.5 g or less, about 4 g or less, about 3.5 g or less, about 3 g or less, about 2.8 g or less, about 2.6 g or less, about 2.4 g or less, about 2.2 g or less, about 2 g or less, about 1.9 g or less, about 1.8 g or less, about 1.7 g or less, about 1.6 g or less, about 1.5 g or less, about 1.4 g or less, about 1.3 g or less, about 1.2 g or less, about 1.1 g or less, about 1 g or less, about 0.9 g or less, about 0.8 g or less, about 0.7 g or less, about 0.6 g or less, about 0.5 g or less, about 0.4 g or less, about 0.3 g or less, about 0.2 g or less, about 0.1 g or less, about 0.08 g or less, about 0.06 g or less, about 0.04 g or less, or about 0.02 g or less, relative to about 100 g of the saccharide-containing composition. These lower and upper limits with respect to the amount of compound of formula (I) can be used in any combination to describe the concentration range of the compound of formula (I), relative to about 100 g of the saccharide containing composition. In a preferred embodiment, the amount of compound of formula (I) is about 0.01 g to about 5 g (more preferably about 0.5 g to about 2 g), relative to about 100 g of the saccharide-containing composition.

Suitable amounts of the compound of formula (I) relative to about 200 ppm of one or more fermentation and/or enzyme inhibitors present in the saccharide-containing composition can be about 0.05 g or more, e.g., about 0.1 g or more, about 0.15 g or more, about 0.2 g or more, about 0.25 g or more, about 0.3 g or more, about 0.35 g or more, about 0.4 g or more, about 0.45 g or more, about 0.5 g or more, about 0.55 g or more, about 0.6 g or more, about 0.65 g or more, about 0.7 g or more, about 0.75 g or more, about 0.8 g or more, about 0.85 g or more, about 0.9 g or more, about 0.95 g or more, about 1 g or more, about 1.2 g or more, about 1.3 g or more, about 1.4 g or more, about 1.5 g or more, about 1.6 g or more, about 1.7 g or more, about 1.8 g or more, about 1.9 g or more, about 2 g or more, about 2.2 g or more, about 2.4 g or more, about 2.6 g or more, about 2.8 g or more, about 3 g or more, about 3.5 g or more, about 4 g or more, about 4.5 g or more, about 5 g or more, about 5.5 g or more, about 6 g or more, about 6.5 g or more, about 7 g or more, about 7.5 g or more, about 8 g or more, about 8.5 g or more, about 9 g or more, or about 9.5 g or more. The maximum amount of compound of formula (I) is not particularly limited but typically will be about 10 g or less, e.g., about 9.5 g or less, about 9 g or less, about 8.5 g or less, about 8 g or less, about 7.5 g or less, about 7 g or less, about 6.5 g or less, about 6 g or less, about 5.5 g or less, about 5 g or less, about 4.5 g or less, about 4 g or less, about 3.5 g or less, about 3 g or less, about 2.8 g or less, about 2.6 g or less, about 2.4 g or less, about 2.2 g or less, about 2 g or less, about 1.9 g or less, about 1.8 g or less, about 1.7 g or less, about 1.6 g or less, about 1.5 g or less, about 1.4 g or less, about 1.3 g or less, about 1.2 g or less, about 1.1 g or less, about 1 g or less, about 0.95 g or less, about 0.9 g or less, about 0.85 g or less, about 0.8 g or less, about 0.75 g or less, about 0.7 g or less, about 0.65 g or less, about 0.6 g or less, about 0.55 g or less, about 0.5 g or less, about 0.45 g or less, about 0.4 g or less, about 0.35 g or less, about 0.3 g or less, about 0.25 g or less, about 0.2 g or less, about 0.15 g or less, or about 0.1 g or less, relative to about 200 ppm of one or more fermentation and/or enzyme inhibitors present in the saccharide-containing composition. These lower and upper limits with respect to the amount of compound of formula (I) can be used in any combination to describe the concentration range of the compound of formula (I), relative to about 200 ppm of one or more fermentation and/or enzyme inhibitors present in the saccharide-containing composition. In a preferred embodiment, the amount of compound of formula (I) is about 0.5 g to about 3 g (more preferably about 0.6 g to about 2 g), relative to about 200 ppm of one or more fermentation and/or enzyme inhibitors present in the saccharide-containing composition. In this context, the amount of compound of formula (I) can be relative to one specific fermentation and/or enzyme inhibitor, as defined herein (e.g., hydroxymethylfurfural or syringaldehyde), that is present in the saccharide-containing composition, or the amount of compound of formula (I) can be relative to the total amount of two or more fermentation and/or enzyme inhibitors, as defined herein (e.g., hydroxymethylfurfural and syringaldehyde), that are present in the saccharide-containing composition.

Suitable amounts of the compound of formula (I) relative to about 200 g of one or more monosaccharides present in 1 L of the saccharide-containing composition can be about 0.01 g or more, e.g., about 0.02 g or more, about 0.06 g or more, about 0.08 g or more, about 0.1 g or more, about 0.12 g or more, about 0.14 g or more, about 0.16 g or more, about 0.18 g or more, about 0.2 g or more, about 0.25 g or more, about 0.3 g or more, about 0.35 g or more, about 0.4 g or more, about 0.45 g or more, about 0.5 g or more, about 0.55 g or more, about 0.6 g or more, about 0.65 g or more, about 0.7 g or more, about 0.75 g or more, about 0.8 g or more, about 0.85 g or more, about 0.9 g or more, about 0.95 g or more, about 1 g or more, about 1.05 g or more, about 1.1 g or more, about 1.15 g or more, about 1.2 g or more, about 1.25 g or more, about 1.3 g or more, about 1.35 g or more, about 1.4 g or more, about 1.45 g or more, about 1.5 g or more, about 1.55 g or more, about 1.6 g or more, about 1.65 g or more, about 1.7 g or more, about 1.75 g or more, about 1.8 g or more, about 1.85 g or more, about 1.9 g or more, about 1.95 g or more, about 2 g or more, about 2.2 g or more, about 2.4 g or more, about 2.6 g or more, about 2.8 g or more, about 3 g or more, about 3.5 g or more, about 4 g or more, about 4.5 g or more, about 5 g or more, about 5.5 g or more, about 6 g or more, about 6.5 g or more, about 7 g or more, about 7.5 g or more, about 8 g or more, about 8.5 g or more, about 9 g or more, or about 9.5 g or more. The maximum amount of compound of formula (I) is not particularly limited but typically will be about 10 g or less, e.g., about 9.5 g or less, about 9 g or less, about 8.5 g or less, about 8 g or less, about 7.5 g or less, about 7 g or less, about 6.5 g or less, about 6 g or less, about 5.5 g or less, about 5 g or less, about 4.5 g or less, about 4 g or less, about 3.5 g or less, about 3 g or less, about 2.8 g or less, about 2.6 g or less, about 2.4 g or less, about 2.2 g or less, about 2 g or less, about 1.95 g or less, about 1.9 g or less, about 1.85 g or less, about 1.8 g or less, about 1.75 g or less, about 1.7 g or less, about 1.65 g or less, about 1.6 g or less, about 1.55 g or less, about 1.5 g or less, about 1.45 g or less, about 1.4 g or less, about 1.35 g or less, about 1.3 g or less, about 1.25 g or less, about 1.2 g or less, about 1.15 g or less, about 1.1 g or less, about 1.05 g or less, about 1 g or less, about 0.95 g or less, about 0.9 g or less, about 0.85 g or less, about 0.8 g or less, about 0.75 g or less, about 0.7 g or less, about 0.65 g or less, about 0.6 g or less, about 0.55 g or less, about 0.5 g or less, about 0.45 g or less, about 0.4 g or less, about 0.35 g or less, about 0.3 g or less, about 0.25 g or less, about 0.2 g or less, about 0.18 g or less, about 0.16 g or less, about 0.14 g or less, about 0.12 g or less, about 0.1 g or less, about 0.08 g or less, about 0.06 g or less, about 0.04 g or less, or about 0.02 g or less, relative to about 200 g of one or more monosaccharides present in 1 L of the saccharide-containing composition. These lower and upper limits with respect to the amount of compound of formula (I) can be used in any combination to describe the concentration range of the compound of formula (I), relative to about 200 g of one or more monosaccharides present in 1 L of the saccharide-containing composition. In a preferred embodiment, the amount of compound of formula (I) is about 0.5 g to about 2.4 g (more preferably about 1 g to about 2 g), relative to about 200 g of one or more monosaccharides present in 1 L of the saccharide-containing composition. In this context, the amount of compound of formula (I) can be relative to one monosaccharide, as defined herein (e.g., glucose or xylose), that is present in the saccharide-containing composition, or the amount of compound of formula (I) can be relative to the total amount of two or more monosaccharides, as defined herein (e.g., glucose and xylose), that are present in the saccharide-containing composition.

The saccharide-containing composition can include additional components, such as, e.g., acetic acid, formic acid, levulinic acid, a uronic acid (e.g., glucuronic acid), and/or phenolic compounds (e.g., vanillin, vanillic acid, homovanillic acid, dihydroconiferyl alcohol, coniferyl aldehyde, hydroquinone, catechol, acetoguaiacone, and 4-hydroxybenazoic acid). The actual components of the saccharide-containing composition will be determined at least in part by the source of the composition and/or the method(s) of processing a feedstock.

The saccharide-containing composition can be a hydrolysis product of any suitable feedstock, typically a biomass feedstock. As used herein, the term "biomass" means a renewable energy source generally comprising carbon-based biological material derived from living or recently-living organisms. Suitable feedstocks include lignocellulosic feedstock, cellulosic feedstock, hemicellulosic feedstock, starch-containing feedstocks, etc. The lignocellulosic feedstock can be from any lignocellulosic biomass, such as plants (e.g., duckweed, annual fibers, etc.), trees (softwood or hardwood, e.g., spruce (Norwegian spruce), elm, oak, aspen, pine, poplar, willow, or eucalyptus), bushes, grass (e.g., miscanthus, switchgrass, rye, reed canary grass, giant reed, or sorghum), dedicated energy crops, municipal waste (e.g., municipal solid waste), and/or a by-product of an agricultural product (e.g., corn, sugarcane, sugar beets, pearl millet, grapes, rice, straw). The biomass can be from a virgin source (e.g., a forest, woodland, or farm) and/or a by-product of a processed source (e.g., off-cuts, bark, and/or sawdust from a paper mill or saw mill, sugarcane bagasse, corn stover, palm oil industry residues, branches, leaves, roots, and/or hemp). Suitable feedstocks may also include the constituent parts of any of the aforementioned feedstocks, including, without limitation, lignin, C6 saccharides (including cellulose, cellobiose, C6 oligosaccharides, and C6 monosaccharides), C5 saccharides (including hemicellulose, C5 oligosaccharides, and C5 monosaccharides), and mixtures thereof.

The feedstock hydrolysis can be performed by any suitable method. Suitable hydrolysis methods include solvothermal processes (e.g., employing hot compressed fluids (e.g., hot compressed water), sub-critical, near-critical or supercritical fluids comprising, consisting of, or consisting essentially of water, or employing mixed sub-, near-, or supercritical fluids comprising, consisting of, or consisting essentially of two or more fluid components, such as water and an alcohol (e.g., ethanol and/or methanol) and/or carbon dioxide or sulfur dioxide), acid hydrolysis (e.g., employing a solid acid catalyst and/or a protic acid, such as hydrochloric acid, sulfuric acid, phosphoric acid, nitric acid, hydroiodic acid, hydrobromic acid, chloric acid, perchloric acid, and p-toluenesulfonic acid), base hydrolysis (e.g., employing a Group I and/or Group II hydroxide, such as lithium hydroxide, sodium hydroxide, potassium hydroxide, rubidium hydroxide, cesium hydroxide, magnesium hydroxide, calcium hydroxide, and barium hydroxide; ammonium hydroxide; and sodium, potassium, and/or calcium carbonate), or enzymatic hydrolysis (e.g., cellulases, xylanases, laccases or peroxidases, such as *Trametes versicolor*). The hydrolysis typically serves to break down the oligosaccharides and/or polysaccharides in the lignocellulosic feedstock into monosaccharides and/or shorter length oligosaccharides. For example, acid hydrolysis can be carried out using mineral acids, such as $H_2SO_4$ or HCl at temperatures of about 120-200° C. Hydrolysis using solvothermal methods (e.g., hydrothermal methods) can be performed in one or two steps at suitable temperatures and pressures. Suitable temperatures for the first and/or second step of a solvothermal process (e.g., hydrothermal hydrolysis process) include temperatures of about 50° C. to about 500° C., and suitable pressures are about 1 bar to about 350 bar. Typically, the pressure is sufficient to maintain the fluid in liquid or supercritical form.

Suitable temperatures for the first and/or second step in a solvothermal process (e.g., hydrothermal hydrolysis process) are about 50° C. or more, e.g., about 60° C. or more, about 70° C. or more, about 80° C. or more, about 90° C. or more, about 100° C. or more, about 110° C. or more, about 120° C. or more, about 130° C. or more, about 140° C. or more, about 150° C. or more, about 160° C. or more, about 170° C. or more, about 180° C. or more, about 190° C. or more, about 200° C. or more, about 210° C. or more, about 220° C. or more, about 230° C. or more, about 240° C. or more, about 250° C. or more, about 260° C. or more, about 270° C. or more, about 280° C. or more, about 290° C. or more, about 300° C. or more, about 310° C. or more, about 320° C. or more, about 330° C. or more, about 340° C. or more, about 350° C. or more, about 360° C. or more, about 370° C. or more, about 380° C. or more, about 390° C. or more, about 400° C. or more, about 410° C. or more, about 420° C. or more, about 430° C. or more, about 440° C. or more, about 450° C. or more, about 460° C. or more, about 470° C. or more, about 480° C. or more, or about 490° C. or more. The maximum temperature for the first and/or second step of a solvothermal process is not particularly limited, but typically will be about 500° C. or less, e.g., about 490° C. or less, about 480° C. or less, about 470° C. or less, about 460° C. or less, about 450° C. or less, about 440° C. or less, about 430° C. or less, about 420° C. or less, about 410° C. or less, about 400° C. or less, about 390° C. or less, about 380° C. or less, about 370° C. or less, about 360° C. or less, about 350° C. or less, about 340° C. or less, about 330° C. or less, about 320° C. or less, about 310° C. or less, about 300° C. or less, about 290° C. or less, about 280° C. or less, about 270° C. or less, about 260° C. or less, about 250° C. or less, about 240° C. or less, about 230° C. or less, about 220° C. or less, about 210° C. or less, about 200° C. or less, about 190° C. or less, about 180° C. or less, about 170° C. or less, about 160° C. or less, about 150° C. or less, about 140° C. or less, about 130° C. or less, about 120° C. or less, about 110° C. or less, about 100° C. or less, about 90° C. or less, about 80° C. or less, about 70° C. or less, or about 60° C. or less. These lower and upper limits with respect to the temperatures of a first and/or second solvothermal process can be used in any combination to describe the temperature range of a solvothermal process (e.g., hydrothermal hydrolysis process) for hydrolyzing a feedstock.

Suitable pressures for the first and/or second step in a solvothermal process (e.g., hydrothermal hydrolysis process) are about 1 bar or more, e.g., about 5 bar or more, about 10 bar or more, about 20 bar or more, about 30 bar or more, about 40 bar or more, about 50 bar or more, about 60 bar or more, about 70 bar or more, about 80 bar or more, about 90 bar or more, about 100 bar or more, about 125 bar or more, about 150 bar or more, about 175 bar or more, about 200 bar or more, about 225 bar or more, about 250 bar or more, about 275 bar or more, about 300 bar or more, or about 325 bar or more. The maximum pressure for the first and/or second step of a solvothermal process is not particularly limited, but typically will be about 350 bar or less, e.g., about 325 bar or less, about 300 bar or less, about 275 bar or less, about 250 bar or less, about 225 bar or less, about 200 bar or less, about 175 bar or less, about 150 bar or less, about 125 bar or less, about 100 bar or less, about 90 bar or less, about 80 bar or less, about 70 bar or less, about 60 bar or less, about 50 bar or less, about 40 bar or less, about 30 bar or less, about 20 bar or less, about 10 bar or less, or about 5 bar or less. These lower and upper limits with respect to the pressures of a first and/or second solvothermal process can be used in any combination to describe the pressure range of a solvothermal process (e.g., hydrothermal hydrolysis process) for hydrolyzing a feedstock.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. (e.g., at least about 100° C., at least about 150° C., at least about 200° C., at least about 250° C.) but typically less than subcritical and at pressures such that water is in a liquid state.

As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc.). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

In any of the foregoing embodiments or other embodiments, the invention provides a compound of formula (I), in which (i) each of $R^1$-$R^4$ is —H, -M, or —$R^7R^8M$; or (ii) two or more of $R^1$-$R^4$ are taken together to be a divalent counterion, a trivalent counterion, or a tetravalent counterion.

The substituent n can be 0 or an integer of 1 to 4 (i.e., 1, 2, 3, or 4). In any of the foregoing embodiments or other embodiments, the invention provides a compound of formula (I), in which n is 1, and X is not —H (i.e., X is a substituent other than —H), such that the diamine compound is mono-substituted. In other aspects, n is 0, and the compound of formula (I) does not include an X substituent.

In certain embodiments, the compound of formula (I) has at least one X substituent. Preferably, at least one X substituent is hydrophilic. In any of the foregoing embodiments or other embodiments, X can be $C_1$-$C_8$ alkyl, aryl, heteroaryl, alkylene oxide, oligoalkylene oxide, polyalkylene oxide, —OM, —$OR^7$, —$R^7OR^8$, —$R^7OM$, —$C(O)OR^7$, —$C(O)R^7$, —$PO_4$, —$PO(OH)_2$, —$PO(OH)(OR^7)$, —$PO(OR^7)_2$, —$SO_3H$, —$SO_3M$, —$R^7SO_3H$, —$R^7SO_3M$, —$R^7SO_3R^8$, —$SR^7$, —$SO_2R^7$, —$NR^7R^8$, —$NR^7R^8R^9M$, or any of the foregoing groups that is optionally substituted.

Specific examples of the compound of formula (I) include m-phenylenediamine, o-phenylenediamine, p-phenylenediamine, 2,4-diaminotoluene, and salts thereof. Preferably, the compound of formula (I) is m-phenylenediamine or a salt thereof.

As used herein, unless otherwise specified, the term "alkyl" means a saturated straight chain or branched non-cyclic hydrocarbon having an indicated number of carbon atoms (e.g., $C_1$-$C_8$, $C_1$-$C_6$, $C_1$-$C_5$, $C_1$-$C_4$, $C_1$-$C_3$, etc.). Representative saturated straight chain alkyls include methyl, ethyl, n-propyl, n-butyl, n-pentyl, n-hexyl, n-heptyl, and n-octyl. Representative saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, and the like. An alkyl group can be unsubstituted or substituted.

As used herein, unless otherwise specified, the term "alkenyl group" means a straight chain or branched non-cyclic hydrocarbon having an indicated number of carbon atoms (e.g., $C_2$-$C_8$, $C_2$-$C_7$, $C_2$-$C_6$, $C_2$-$C_5$, $C_2$-$C_4$, $C_2$-$C_3$, etc.) and including at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, and the like. Any unsaturated group (double bond) of an alkenyl can be unconjugated or conjugated to another unsaturated group. An alkenyl group can be unsubstituted or substituted.

The term "cycloalkyl," as used herein, means a cyclic alkyl moiety containing from, for example, 3 to 8 carbon atoms, preferably from 5 to 6 carbon atoms. Examples of such moieties include cyclopropyl, cyclobutyl, cyclopentyl, cyclohexyl, cycloheptyl, cyclooctyl, and the like. A cycloalkyl group can be unsubstituted or substituted.

The team "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, preferably from 6 to 18 carbon atoms, more preferably from 6 to 14 carbon atoms and most preferably from 6 to 10 carbon atoms. It is understood that the term aryl includes carbocyclic moieties that are planar and comprise 4n+2 π electrons, according to Hückel's Rule, wherein n=1, 2, or 3. When an aryl group is substituted with a substituent as described herein, the aromatic ring hydrogen is replaced with the substituent, and this replacement can take place in any of the available hydrogens, e.g., 2, 3, 4, 5, and/or 6-position wherein the 1-position is the point of attachment of the aryl group in the compound of the present invention.

The term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring, but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, pyrrolyl, thienyl, isothiazolyl, thiazolyl, isoxazolyl, and oxadiazolyl. A heteroaryl group can be unsubstituted or substituted.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. Preferably, a heterocycloalkyl is a 5, 6, or 7-membered monocyclic ring and contains one, two, or three heteroatoms selected from nitrogen, oxygen, and/or sulfur. The heterocycloalkyl may be attached to the parent structure through a carbon atom or through any heteroatom of the heterocycloalkyl that results in a stable structure. Examples of such heterocycloalkyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl. A heterocycloalkyl group can be unsubstituted or substituted.

The team "halo" refers to a halogen selected from fluorine, chlorine, bromine, and iodine, preferably fluorine, chlorine, or bromine.

As used herein, unless otherwise specified, a group that is "substituted" means that the group has one or more substituents (e.g., 1, 2, 3, 4, 5, 6, etc.), such as alkyl, alkenyl, alkynyl, cycloalkyl, aroyl, halo, haloalkyl (including trifluoromethyl), haloalkoxy (including trifluoromethoxy), hydroxy, alkoxy, cycloalkyloxy, heterocylooxy, oxo (=O), alkanoyl, aryl, arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, alkanoylamino, aroylamino, aralkanoylamino, substituted alkanoylamino, substituted arylamino, substituted aralkanoylamino, thiol (mercapto), alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido (e.g., —SO$_2$NH$_2$), substituted sulfonamido, nitro, cyano, carboxy, carbamido, carbamyl (e.g., —CONH$_2$), substituted carbamyl (e.g., —CONH-alkyl, —CONH-aryl, —CONH-arylalkyl, or instances where there are two substituents on the nitrogen selected from alkyl or arylalkyl), alkoxycarbonyl, aryl, substituted aryl, substituted or unsubstituted heterocycloalkyl, and substituted or unsubstituted heteroaryl.

As used herein, the term "alkylene oxide" refers to an alkylene moiety comprising at least two oxygens (e.g., ethylene glycol, propylene glycol, etc.). The alkylene oxide can be in a monomeric form or as an oligoalkylene oxide or polyalkylene oxide. The alkylene oxide (or a repeat unit thereof) can have any number of suitable carbons, such as $C_2$, $C_3$, $C_4$, $C_5$, $C_6$) $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$. The alkylene oxide can contain repeat units that are all the same (i.e., each repeat unit has the same number of carbon atoms and can be considered a "homo alkylene oxide" akin to a homopolymer or homooligomer), or the alkylene oxide can contain repeat units that are not all the same (i.e., some or all of the repeat units may be different from each other, and this type of alkylene oxide can be considered a "hetero alkylene oxide" akin to a heteropolymer or heterooligomer). Preferably, the number of carbons in the repeat unit of the alkylene oxide is determined by the desired solubility properties. For example, it will generally be understood that the longer the alkylene portion of the alkylene oxide repeat unit(s), the less water soluble the alkylene oxide (and therefore the compound that it is attached to) will be. Inversely, the shorter the alkylene portion of the alkylene oxide repeat unit(s), the more water soluble the alkylene oxide (and therefore the compound that it is attached to) will be.

In some aspects, the alkylene oxide comprises a propylene ($C_3$) oxide, an ethylene ($C_2$) oxide, or both propylene oxide and ethylene oxide units. The alkylene oxide can be linked to any suitable number of alkyl and/or alkylene oxide primary branches. Preferably, the length of the alkyl branches and the number of primary branches is determined by the desired solubility properties. In certain aspects, the alkylene oxide comprises at least 2 (e.g., at least 3, at least 4, at least 4, at least 5, at least 6, at least 7, or at least 8) primary branches. There can be an upper limit of any number of suitable branches, e.g., up to 100 (e.g., up to 80, up to 60, up to 40, up to 20, or up to 10) alkyl and/or alkylene oxide primary branches. These lower and upper limits with respect to the number of alkyl and/or alkylene oxide primary branches can be used in any combination (e.g., 2-100, 3-80, and 4-10, etc.). In certain aspects, the alkylene oxide has 2 to 20 primary branches. Preferably, the alkylene oxide backbone is linked to 4 to 8 primary branches (e.g., ethylene oxide primary branches). Depending on the number and placement of branches, the polyalkylene oxide can be described as a star polymer, comb polymer, brush polymer, palm tree polymer, H-shaped polymer, or dumbbell polymer.

In some embodiments, the oligoalkylene oxide, polyalkylene oxide, or primary branch can be based on polyethylene glycol (PEG). For example, a branched PEG, e.g., an alkylene oxide backbone comprising 2 to 100 PEG branches, can be used in accordance with an embodiment. A polymer comprising 3 to 10 (e.g., 3, 4, 5, 6, 7, 8, 9, or 10) PEG branches is a preferred embodiment.

As used herein, the counterion M is any suitable positively or negatively charged moiety that serves to neutralize the charge of a group, as described herein. Whether the counterion M is positively or negatively charged will be clear when viewed in the context of the relevant disclosure herein. In certain aspects, M is a monovalent anion, which includes, e.g., a halide (e.g., $Cl^-$, $F^-$, $Br^-$, or $I^-$), $OH^-$, $CH_3COO^-$, $HCOO^-$, $HCO_3^-$, $HC_2O_4^-$, $NO_2^-$, $NO_3^-$, $NH_2^-$, $MnO_4^-$, $ClO_2^-$, $ClO_2^-$, $ClO_3^-$, $ClO_4^-$, $IO^-$, $IO_3^-$, $IO_4^-$, $BrO^-$, $BrO_3^-$, $HSO_3^-$, $HSO_4^-$, $H_2PO_4^-$, $HS^-$, $SCN^-$, or $CN^-$. In certain other aspects, M is a monovalent cation, which includes a Group I cation (e.g., $Li^+$, $Na^+$, $K^+$, $Rb^+$, or $Cs^+$), a metal cation (e.g., $Ag^+$, $Au^+$, or $Cu^+$), or a quaternary ammonium group, which can have the formula $—N^+R^{11}R^{12}R^{13}$, in which substituents $R^{11}$, $R^{12}$, and $R^{13}$ are independently selected from hydrogen, alkyl, alkenyl, cycloalkyl, and aryl, as described herein.

In any of the embodiments above, whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, 4-12 carbon atoms, etc., as appropriate).

In any of the embodiments above, the phrase "salt" is intended to include salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used.

In any of the foregoing embodiments, the substituent $—NR^3R^4$ can be attached to the phenyl ring in formula (I) at any suitable position (e.g., the 2-, 3-, 4- or 5-position) relative to the amino group $—NR^1R^2$. In certain embodiments, $—NR^3R^4$ is attached at the 2-, 3-, or 4-position. Preferably, $—NR^3R^4$ is attached at the 3-position.

In any of the foregoing embodiments or other embodiments, when n is 1, 2, 3, or 4, each X can be present in formula (I) at any suitable position on the phenyl ring (e.g., the 2-, 3-, 4- or 5-position) relative to the amino group $—NR^1R^2$. In certain embodiments, X is present in formula (I) at the 2- and/or 4-positions.

The method can further comprise adjusting the pH of the composition to about 5-9 before contacting the composition with the compound of formula (I). Adjusting the pH can be done by any suitable method, but typically involves adding an appropriate amount of acid and/or base, as needed, to provide the desired pH. Suitable bases include Group I and Group II hydroxides (e.g., lithium hydroxide, sodium hydroxide, potassium hydroxide, rubidium hydroxide, cesium hydroxide, magnesium hydroxide, calcium hydroxide (lime), and barium hydroxide), ammonium hydroxide, and sodium carbonate (soda ash). Suitable acids include inorganic acids (e.g., hydrochloric acid, sulfuric acid, phosphoric acid, nitric acid, hydroiodic acid, hydrobromic acid, chloric acid, and perchloric acid), organic acids (e.g., acetic acid, oxalic acid, carbonic acid, p-toluenesulfonic acid, and tartaric acid), sulfur dioxide, and carbon dioxide. The pH can be measured by any suitable means, such as litmus paper, pH indicator tape or paper, liquid indicators, or a pH meter.

In some embodiments, the composition is not subjected to any chemical, physical, or biological methods to reduce the fermentation inhibitor and/or enzyme inhibitor content prior to fermentation and/or enzymatic treatments, other than contacting the composition with a compound of formula (I). Such methods include, for example, overliming, treatment with alkali (e.g., sodium hydroxide, calcium oxide, or calcium hydroxide), treatment with activated charcoal, treatment with ion-exchange resins, and treatment with an enzyme laccase and/or fungus (e.g., *Trichoderma reesei*). In some embodiments, the composition is not subjected to an overliming step (e.g., contacting the composition with calcium oxide or calcium hydroxide as a means to reduce the fermentation inhibitor and/or enzyme inhibitor content).

In some aspects, the method can optionally further comprise transforming at least a portion of the composition by a transformation selected from a catalytic treatment, a biocatalytic treatment, a non-catalytic treatment, an enzymatic treatment, and a combination thereof before, during, or after contacting the composition with the compound of formula (I). If necessary, the pH of the composition can be adjusted before or after the transformation as described herein. In some aspects, the transformation is a fermenting step to produce a fermentation product (e.g., a biofuel, acid (e.g., succinic acid, lactic acid, acrylic acid, levulinic acid, etc.), or other chemicals, such as furfural and/or xylitol), as described herein. Typically, the transforming step involves the use of a microbial biocatalyst, enzyme, yeast (e.g., *Saccharomyces cerevisiae, Kluyveromyces lactis, Kluyveromyces lipoltyica, Schizosaccharomyces pombe, Pichia stipitis, Clostridium acetobutylicum*, or *Debaromyces hansenii*), and/or bacteria (e.g., *Zymomonas mobilis*). In a preferred embodiment, the transforming step involves yeast or a catalyst.

As used herein, "transformed enzymatically" or "enzymatic transformation" means that the transformation (e.g., reaction) is effected by one or more enzymes, or by proteins or polypeptides having enzymatic activity (i.e., activity similar to that of a bona fide enzyme).

As used herein, "transformed catalytically" or "catalytic transformation" means that the transformation (e.g., reaction) is effected by a catalyst or other agent having catalytic activity (e.g., acid, base, metal, and the like).

As used herein, "transformed non-catalytically" or "non-catalytic transformation" means that the transformation (e.g., reaction) is effected by a reactant or reagent that is consumed in the reaction.

As used herein, "transformed biocatalytically" or "biocatalytic transformation" means that the transformation is effected by one or more organisms (e.g., bacteria, yeast, algae, and the like).

Desirably, the transforming step results in the production of a least one biofuel, such as a bioalcohol and/or biodiesel. Bioalcohols include ethanol and butanol. Biodiesel includes long chain alkyl(methyl, ethyl, and/or propyl) esters, such as fatty acid methyl esters (FAMEs). Preferably, the biofuel produced is ethanol.

If desired, the compound of formula (I) can be used in combination with a polymer or solid support to form a complex. In particular, the compound can be associated with the polymer or solid support by any desired mechanism (e.g., incorporated into or onto, embedded in, complexed to, covalently bound to, electrostatically bound to, and/or grafted to the polymer or solid support). In some aspects, the complex comprising a compound of formula (I) and a polymer or solid support is employed to enable facile removal of the compound of formula (I) from the saccharide-containing composition. The polymer and solid support can be used in or derived from any suitable form, such as, for example, a bead, microparticle, nanoparticle, microarray, pellet, powder, dust, foam, aggregate, amorphous solid, sheet, film, resin, packed bed, metal-organic framework (MOF), covalent organic framework (COF), coating on a substrate, membrane, woven or nonwoven fibrous web, fiber, filter, tube, fabric, or the like.

The polymer can be any suitable polymer, including natural or synthetic. Synthetic polymer substrates suitable for use in the invention include, for example, polyvinylpyrrolidone, acrylics, polyacrylate, poly(methyl methacrylate) (PMMA), acrylonitrile-butadiene-styrene, polyacrylonitrile, acetals, polyphenylene oxides, polyimides, polystyrene, polypropylene, polyethylene, polybutylene, polytetrafluoroethylene, polyvinylidene fluoride, polyvinyl chloride, polyethylenimine, polyesters (e.g., polyethylene terephthalate, or polybutylene terephthalate), polyvinyl alcohol, polyethers, polyamide (e.g., nylon), polydimethylsiloxane (PDMS), polyorthoester, polyanhydride, polysulfone, polyether sulfone, polycaprolactone, polyhydroxy-butyrate valerate, polylactones, polyurethanes, polycarbonates, polylactone, rubber, silicone rubber, and latex, as well as copolymers and combinations thereof. Suitable natural polymers include cellulose, cotton, wool, natural rubber, agarose, dextran, natural latex, and combinations thereof. Typical rubber substrates suitable for use in the invention include, for example, silicones, fluorosilicones, nitrile rubbers, silicone rubbers, polyisoprenes, sulfur-cured rubbers, butadiene-acrylonitrile rubbers, isoprene-acrylonitrile rubbers, and the like.

If desired, the polymer can be characterized quantitatively using known methods, including gel permeation chromatography (also known as size exclusion chromatography and gel filtration chromatography), nuclear magnetic resonance spectroscopy (NMR), matrix-assisted laser desorption/ionization mass spectroscopy (MALDI), light scattering (e.g., low angle and multi angle), small angle neutron scattering (SANS), sedimentation velocity, end group analysis, osmometry, cryoscopy/ebulliometry, and viscometry. The polymer can be any suitable average molecular weight, which usually is a function of the ratio of starting materials and synthesis method. For example, the number, weight, or volume average molecular weight can be at least about 200 g/mol (e.g., at least about 300 g/mol, at least about 500 g/mol, at least about 800 g/mol, at least about 1,000 g/mol, at least about 1,500 g/mol, or at least about 2,000 g/mol) and/or up to about 100,000 g/mol (e.g., up to about 90,000 g/mol, up to about 80,000 g/mol, up to about 70,000 g/mol, up to about 60,000 g/mol, up to about 50,000 g/mol, up to about 40,000 g/mol, up to about 30,000 g/mol, up to about 20,000 g/mol, or up to about 10,000 g/mol). These lower and upper limits with respect to the number, weight, or volume average molecular weight can be used in any combination to describe the polymer molecular weight range (e.g., about 200 to about 100,000 g/mol, about 300 g/mol to about 50,000 g/mol, about 1,000 to about 20,000 g/mol, etc.).

The solid support can be of any suitable material, including glass, carbon, zeolite (including synthetic zeolites, such as aluminosilicate and natural zeolites, such as analcime, chabazite, clinoptilolite, heulandites, natrolite, phillipsite, and stilbite), inorganic oxide (e.g., silica, alumina, titania, ceria, or mixed oxides of the elements silicon, aluminum, calcium, magnesium, and titanium), metal (e.g., gold, platinum, silver, copper, nickel, aluminum, iron oxide, and combinations thereof), or any combination thereof (e.g., combinations of organic and inorganic components, as in MOFs).

In certain aspects, the polymer has a reactive functional group on the terminal end of the polymer or as a group pendant to the polymer backbone. Additionally, the solid support preferably has a reactive functional group on its surface. The functional group can be, for example, amino, ammonium, hydroxyl, mercapto, sulfone (e.g., —$RSO_2R'$), sulfinic acid (e.g., —RSO(OH)), sulfonic acid (e.g., —$RSO_2$(OH)), thiocyanate, thione, thial (e.g., —C(S)H or —RC(S)H), carboxyl, halocarboxy (e.g., —OC(O)Hal), halo, imido, anhydrido, alkenyl, alkynyl, phenyl, benzyl, carbonyl, formyl, haloformyl (e.g., —RC(O)X), carbonato, ester, alkoxy, phenoxy, hydroperoxy, peroxy, ether, glycidyl, epoxy, hemiacetal (e.g., —OCH(R)OH or —CH(OR)OH)), hemiketal (e.g., —OCRR'OH or —CR(OR')OH), acetal (e.g., —OCHR(OR') or —CH(OR)(OR')), ketal (e.g., —OCRR' (OR") or —CR(OR')(OR")), orthoester, orthocarbonate ester, amido (e.g., —C(O)NRR' or —NRC(O)R'), imino, imido, azido, azo, cyano, nitrato, nitrilo, nitrito, nitro, nitroso, pyridinyl, phosphinyl, phosphonic acid, phosphate, phosphoester, phosphodiester, boronic acid, boronic ester, borinic acid, bonnie ester, or a combination thereof. In the foregoing examples, R, R', and R" are H, alkyl, or cycloalkyl as described herein, and Hal is halo.

In certain aspects, if the polymer or solid support does not have an appropriate functional group to covalently attach to the compound of formula (I), the compound of formula (I) can be associated with the polymer or solid support via non-covalent interactions. Examples of suitable non-covalent interactions include hydrogen bonding, pi-pi stacking, Van der Waals forces, electrostatic, and the like. Such non-covalent interactions can be specific (e.g., hydrogen bonding), non-specific (Van der Waals forces), or any combination thereof.

In certain aspects, if the polymer or solid support does not have an appropriate functional group, the polymer or solid support can be modified to provide a reactive functional group capable of reacting with (e.g., forming a covalent bond with) the compound of formula (I). Typically a suitable functional group can be provided by a chemical transformation, such as, but not limited to, hydrolysis, oxidation (e.g., using Collins reagent, Dess-Martin periodinane, Jones reagent, and potassium permanganate), reduction (e.g., using sodium borohydride or lithium aluminum hydride), alkylation, deprotonation, electrophilic addition (e.g., halogenation, hydrohalogenation, or hydration), hydrogenation, esterification, elimination reaction (e.g., dehydration), nucleophilic substitution, radical substitution, or a rearrangement reaction. If needed, more than one chemical transformation can be used to provide a suitable functional group on the polymer or solid support. Alternatively, a monomer with a desired functional group can be grafted to the solid support.

In preferred embodiments, the reactive functional group is hydroxy, mercapto, or amino. In some aspects, the hydroxy, mercapto, or amino group is present on the surface of the solid support, whereas in other aspects, the hydroxy, mercapto, or amino group is formed on the polymer or solid support by a chemical transformation. In an example, a polymer or solid support comprising an alkenyl group can undergo an acid catalyzed hydration reaction to form a secondary alcohol with a free hydroxy group.

In certain embodiments, to form a covalent bond, the compound of formula (I) preferably includes, or is modified to include, at least one functional group that will react with the functional group on the polymer or solid support. The functional group on the compound of formula (I) can be the same type of moiety described with respect to polymer or solid support. As with the solid support, the functional group can either be present on the compound of formula (I) or formed on the compound via a chemical transformation as described herein for modifying the polymer and solid support.

The complex comprising the compound of formula (I) and a polymer or solid support can be formed by any suitable method using suitable temperatures (e.g., room temperature or reflux), reaction times, solvents, catalysts, and concentrations. In some aspects, an excess amount of the compound of formula (I) will be used to ensure an effective amount of compound is associated with/complexed to/bound to the polymer or solid support.

The method and the various embodiments described herein provide several advantages. In comparison with a conventional overliming process, the inventive method does not require an elevated temperature (e.g., 60° C.) or excessive shaking (e.g., 200 rpm) in order to reduce the aldehyde content of the saccharide-containing composition. Instead, the inventive method readily takes place at room temperature (e.g., about 25° C.) with moderate shaking (e.g., 50 rpm or less). Because solid gypsum is not formed as a by-product of the inventive method, no filtration is required at the end of the process. Moreover, there is reduced sugar degradation when contacting the composition with a compound of formula (I), as compared to an overliming step, as a result of the neutral pH. For example, as the pH is increased from 5 to 7 with sodium hydroxide and back to pH 5 with sulfuric acid, the sodium and sulfur concentrations are lower as compared to the concentrations of these compounds in a conventional overliming step. Each of these process steps represents a savings of time, cost, and/or resources as the inventive method provides an improved efficiency in the preparation of feedstocks in the production of biofuel and other bio-derived chemicals.

In an aspect, the invention provides a compound of formula (I) or a salt thereof

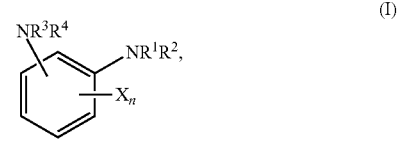

wherein
(1) $R^1$-$R^4$ are the same or different and each is independently selected from —H, -M, $C_1$-$C_8$ alkyl, $C_2$-$C_8$ alkenyl, $C_3$-$C_6$ cycloalkyl, aryl, heteroaryl, alkylene oxide, oligoalkylene oxide, polyalkylene oxide, —$R^7OR^8$, —$R^7OM$, —$CONH_2$, —$R^7CONH_2$, —CONHOH, —$R^7CONHOH$, —$C(O)OR^7$, —$R^8C(O)OR^7$, —C(O)OM, —$R^7C(O)OM$, —$C(O)R^7$, —$R^8C(O)R^7$, —$C(O)N(R^7)R^8$, —$R^9C(O)N(R^7)R^8$, —$C(O)NR^7SO_2N(R^8)R^9$, —$R^{10}C(O)NR^7SO_2N(R^8)R^9$, —$R^7PO_4$, —$R^7PO(OH)_2$, —$R^7PO(OH)(OR^8)$, —$R^7PO(OR^8)_2$, —$R^7SO_3H$, —$R^7SO_2NR^8OH$, —$R^7SR^8$, —$R^7SOR^8$, —$R^7SO_2R^8$, —$R^7SO_2NR^8(R^9)$, —$R^7SO_2NR^8CON(R^9)R^{10}$, —$R^7NO_2$, —$R^7NR^8R^9$, —$R^7NR^8C(O)R^9$, —$R^7N(R^8)C(O)R^9$, —$R^7NR^8SO_2R^9$, —$R^7N(R^8)SO_2R^9$, —$R^7NR^8R^9R^{10}M$, —$R^7R^8M$, and any of the foregoing groups other than —H that is optionally substituted; or any two of $R^1$-$R^4$ taken together is a divalent counterion, and the other two of $R^1$-$R^4$ is defined as in (1); or any three of $R^1$-$R^4$ taken together is a trivalent counterion, and the other one of $R^1$-$R^4$ is defined as in (1); or any two of $R^1$-$R^4$ taken together is a divalent counterion, and the other two of $R^1$-$R^4$ is the same or a different divalent counterion; or all of $R^1$-$R^4$ taken together is a tetravalent counterion;

(2) each X is the same or different and each is independently selected from —H, —OH, $C_1$-$C_8$ alkyl, $C_2$-$C_8$ alkenyl, $C_3$-$C_6$ cycloalkyl, aryl, heteroaryl, alkylene oxide, oligoalkylene oxide, polyalkylene oxide, heterocycloalkyl, $C_1$-$C_8$ haloalkyl, halo, —CN, —$R^7CN$, —$NO_2$, —$R^7NO_2$, —$OR^7$, —$R^7OR^8$, —$OR^7OR^8$, —OM, —$R^7OM$, —$CONH_2$, —$R^7CONH_2$, —CONHOH, —$R^7CONHOH$, —$C(O)OR^7$, —$R^8C(O)OR^7$, —C(O)OM, —$R^7C(O)OM$, —$C(O)R^7$, —$R^8C(O)R^7$, —$C(O)N(R^7)R^8$, —$R^9C(O)N(R^7)R^8$, —$C(O)NR^7SO_2N(R^8)R^9$, —$R^{10}C(O)NR^7SO_2N(R^8)R^9$, —$PO_4$, —$R^7PO_4$, —$PO(OH)_2$, —$R^7PO(OH)_2$, —$PO(OH)(OR^7)$, —$R^8PO(OH)(OR^7)$, —$PO(OR^7)_2$, —$R^8PO(OR^7)_2$, —$SO_3H$, —$SO_3M$, —$R^7SO_3H$, —$R^7SO_3M$, —$R^7SO_3R^8$, —$SO_2NR^7OH$, —$R^8SO_2NR^7OH$, —$SR^7$, —$R^8SR^7$, —$SOR^7$, —$R^8SOR^7$, —$SO_2R^7$, —$R^8SO_2R^7$, —$SO_2NR^7(R^8)$, —$R^9SO_2NR^7(R^8)$, —$SO_2NR^7CON(R^8)R^9$, —$R^{10}SO_2NR^7CON(R^8)R^9$, —$NR^7R^8$, —$R^9NR^7R^8$, —$NR^7C(O)R^8$, —$R^9NR^7C(O)R^8$, —$N(R^7)C(O)R^8$, —$R^9N(R^7)C(O)R^8$, —$NR^7SO_2R^8$, —$R^9NR^7SO_2R^8$, —$N(R^7)SO_2R^8$, —$R^9N(R^7)SO_2R^8$, —$NR^7R^8R^9M$, —$R^{10}NR^7R^8R^9M$, and any of the foregoing groups other than —H that is optionally substituted; or two X substituents can be taken together with the carbon atoms to which they are attached to form a 5- or 6-membered aryl, cycloalkyl or heterocycloalkyl comprising 1 or 2 heteroatoms selected from the group consisting of N, O, and S; and (3) $R^7$, $R^8$, $R^9$, and $R^{10}$ are the same or different and each is independently selected from —H, $C_1$-$C_8$ alkyl, $C_3$-$C_6$ cycloalkyl, aryl, heteroaryl, alkylene oxide, oligoalkylene oxide, polyalkylene oxide, and any of the foregoing groups other than —H that is optionally substituted; and (4) M is a monovalent counterion; and (5) n is 0 or an integer of 1 to 4 for adding to a composition comprising a saccharide and an aldehyde to reduce the aldehyde content in the composition.

The composition components, including the saccharide, aldehyde, and compound of formula (I), are as described herein.

The following examples further illustrate the invention but, of course, should not be construed as in any way limiting its scope.

Example 1

This example demonstrates the ability of a compound of formula (I) to reduce the HMF content of a saccharide-containing composition in an embodiment.

Sugar liquor was prepared by a two-step hydrolysis process with subsequent refining. A slurry of particulate biomass was first subjected to a first hydrolysis step at about 190-240° C. and 50-80 bar for 1-120 min. The resulting solids were subjected to supercritical or near-critical water conditions at about 374-450° C. and 221-300 bar for less than 1 minute. The resulting liquid portion was concentrated to about 250-300 g/L of monomer sugar equivalent and acid hydrolyzed at about 100-200° C. for 1 hour. The acid-hydrolyzed liquor was filtered and neutralized with sodium hydroxide to a pH of about 5-7. After that, the liquid portion was overlimed with calcium oxide at pH of about 8-10 and filtered. The final pH adjustment to about 5-7 was done with 70% sulfuric acid. Overliming was performed to produce the sugar liquor used in these examples, and an aldehyde compound, HMF, subsequently re-added to simulate a sugar liquor that is not overlimed.

The pH of 100 g of the sugar liquor was adjusted to 6 with sodium hydroxide prior to addition of the amine. 1 g of m-phenylenediamine (MPD) was added to the sugar liquor, and the mixture was shaken for 1 hour. The composition of the sugar liquor before contact with MPD and after contact with MPD is set forth in Table 1.

TABLE 1

| Composition | Glucose (g/l) | Xylose (g/l) | Acetic Acid (g/l) | HMF (g/l) |
|---|---|---|---|---|
| Sugar liquor (before contact with MPD) | 155.22 | 23.02 | 1.83 | 10.35 |
| Sugar liquor (after contact with MPD) | 149.44 | 23.22 | 1.99 | 1.50 |

As shown in Table 1, after contacting a saccharide-containing composition, the concentration of aldehyde was reduced to about 1.5 g/L.

Example 2

This example demonstrates the ability of a compound of formula (I) to reduce the syringaldehyde content of a saccharide-containing composition in an embodiment.

To produce a xylose monomer stream a slurry of particulate biomass was subjected to a hydrolysis step at about 190-240° C. and 50-80 bar for about 1-120 min. The resulting liquid fraction was separated from the solid fraction, and the resulting liquid portion was concentrated to about 250-300 g/L of monomer sugar equivalent and acid hydrolyzed at about 100-200° C. for 1 hour. The acid-hydrolyzed liquor was filtered and then neutralized with sodium hydroxide to a pH of about 5-7 to produce the xylose monomer stream.

Five samples labeled Samples 1-5 were evaluated as described in Table 2. Sample 1 was an untreated control. For Samples 2 and 5, the pH of 100 g of the xylose monomer stream was adjusted to 6 with NaOH. Then 1 g of $NaBH_4$ (Sample 2) or 1 g of MPD (Sample 5) was added to the material. The flask was shaken for 30-60 min, and Samples 2 and 5 were then analyzed for syringaldehyde by GC/MS. For Sample 3, the pH of 100 g of the xylose monomer stream was adjusted to 5-6 with $NH_4OH$, and then the pH was further adjusted to about with $Ca(OH)_2$ (overlime step). The flask was shaken for about 30-60 min, adjusted to pH of about 5 with $H_2SO_4$, and then filtered. The resulting liquid portion was analyzed by GC/MS. For Sample 4, the pH of 100 g of the xylose monomer stream was adjusted to 5-6 with $NH_4OH$, the flask was shaken for 30-60 min, and then the samples were analyzed by GC/MS.

The concentrations of syringaldehyde of the various treated xylose monomer streams are set forth in Table 2.

TABLE 2

| Sample | Conditions | Syringaldehyde (ppm) |
|---|---|---|
| 1 | Untreated (control) | 321.5 |
| 2 | $NaBH_4$ | 218.4 |
| 3 | $NH_4OH$ + overlime | 20.2 |
| 4 | $NH_4OH$ | 147.7 |
| 5 | MPD | Not detected |

The target level of syringaldehyde to be considered a "pass" (i.e., a satisfactory test result) is less than about 50 ppm. The analyses shown in Table 2 demonstrate that MPD reduced the amount of syringaldehyde from about 321.5 ppm to below detectable levels within about 1 hour. $NaBH_4$ alone (Sample 2) or $NH_4OH$ alone (Sample 4) did not reduce the concentration of syringaldehyde to below a detectable level. The combination of $NH_4OH$ and overliming (Sample 3) provided a low level of syringaldehyde, most likely due to the industry standard overliming step. Surprisingly, MPD reduced the syringaldehyde to a level that is lower than industry standard overliming was able to achieve.

For fermentation testing, the pH was adjusted back to 5 with $H_2SO_4$ and fermentation was performed with the xylose fermenting organism *Pichia stipitis*. The results are set forth in Table 3. These results confirm that Sample 5, which was treated with MPD, is fermentable.

TABLE 3

| Fermentation time (hr) | Xylose (g/l) | Glucose (g/l) | Acetic Acid (g/l) | HMF (g/l) | Ethanol (g/l) |
|---|---|---|---|---|---|
| 0 | 54.48 | 7.93 | 1.37 | <DL | <DL |
| 24 | 52.23 | 7.10 | 0.92 | 0.18 | <DL |
| 48 | 49.56 | 4.28 | 0.88 | <DL | 1.80 |
| 72 | 44.57 | 2.86 | 0.91 | <DL | 4.86 |
| 96 | 33.19 | 2.14 | 0.70 | <DL | 8.22 |

DL: detection limit

Example 3

This example demonstrates the ability of a compound of formula (I) to reduce the HMF content of a saccharide-containing composition in an embodiment.

Using the same procedure to prepare the sugar liquor as described in Example 1, the pH of 100 g of the sugar liquor was adjusted to 6 with NaOH prior to addition of the amine. For each sample, 1 g of amine was added, and the mixture was shaken for 1 hour. The composition of the sugar liquor of each sample before and after contact with a compound of formula (I) is set forth in Table 4.

TABLE 4

| Composition | Glucose (g/l) | Xylose (g/l) | Acetic Acid (g/l) | HMF (g/l) |
|---|---|---|---|---|
| Sugar liquor (before contact) | 180.58 | 24.76 | 1.45 | 8.44 |
| Sugar liquor (after contact with 2,4-diaminotoluene (DAT)) | 158.80 | 21.30 | 1.34 | 0.74 |
| Sugar liquor (after contact with o-phenylenediamine (OPD)) | 156.03 | 20.62 | 1.39 | <DL |
| Sugar liquor (after contact with p-phenylenediamine (PPD)) | 154.69 | 20.93 | 1.49 | 3.40 |

DL: detection limit

As shown in Table 4, after contacting a saccharide-containing composition with a compound of formula (I), the concentration of aldehyde was reduced.

Example 4

This example demonstrates the ability of a compound of formula (I) to reduce the aldehyde content of a saccharide-containing composition to below inhibitory levels to allow all treated samples to pass a fermentation test in an embodiment.

The saccharide-containing compositions of Examples 1 and 3 were subjected to a fermentation test with the yeast *Saccharomyces cerevisiae*. In the fermentation test, 1% yeast extract and 2% peptone were added to the saccharide-containing compositions of Examples 1 and 3 as growth nutrients, and these compositions were then inoculated with 5% inoculum of *Saccharomyces cerevisiae* (optical density 10). If more than 80% of sugars were consumed in 72 hours of fermentation, the test is considered a "pass" (i.e., a satisfactory test result). The results of the fermentation tests over time are set forth in Table 5.

All of the samples treated with a compound of formula (I) reduced HMF below inhibitory levels at some time point and passed the fermentation test.

Comparative Example 1

This comparative example demonstrates the inability of amines that are not the compound of formula (I) to reduce the aldehyde content of a saccharide-containing composition.

Using the same procedure to prepare the sugar liquor as described in Example 1, the pH of 100 g of the sugar liquor was adjusted to 6 with sodium hydroxide prior to addition of the amine. For each sample, 1 g of amine was added, and the mixture was shaken for 1 hour. The composition of the sugar liquor before and after contact with the amine is set forth in Table 6.

TABLE 6

| Trial | Composition | Glucose (g/l) | Xylose (g/l) | Acetic Acid (g/l) | HMF (g/l) |
|---|---|---|---|---|---|
| 1 | Sugar liquor (before contact) | 178.30 | 24.71 | 1.53 | 8.78 |
| 1A | Sugar liquor (after contact with ethanolamine) | 155.94 | 21.37 | 1.50 | 6.01 |
| 1B | Sugar liquor (after contact with methyl-diethanolamine) | 156.98 | 21.72 | 1.56 | 7.04 |
| 1C | Sugar liquor (after contact with urea) | 159.33 | 22.10 | 1.56 | 7.44 |
| 1D | Sugar liquor (after contact with piperidine) | 156.87 | 21.63 | 1.55 | 6.13 |
| 1E | Sugar liquor (after contact with melamine) | 159.77 | 21.79 | 1.40 | 7.52 |
| 2 | Sugar liquor (before contact) | 180.58 | 24.76 | 1.45 | 8.44 |
| 2A | Sugar liquor (after contact with aniline) | 165.00 | 22.78 | 1.42 | 7.43 |

As shown in Table 6, after contacting a saccharide-containing composition with an amine that is not a compound of formula (I), the concentration of aldehyde was not appreciably reduced, and was not reduced to a non-inhibitory level.

The saccharide-containing compositions were subjected to a fermentation test with the yeast *Saccharomyces cerevisiae*. In the fermentation test, 1% yeast extract and 2% peptone were added to the saccharide-containing compositions as

TABLE 5

| Composition (time) | Glucose (g/l) | Xylose (g/l) | Acetic Acid (g/l) | HMF (g/l) | Ethanol (g/l) | % Glucose Consumed |
|---|---|---|---|---|---|---|
| Sugar Liquor (before contact with amine) | 180.58 | 24.76 | 1.45 | 8.44 | <DL | 0 |
| DAT (0 hr) | 158.80 | 21.30 | 1.34 | 0.74 | <DL | 0 |
| DAT (24 hr) | 76.93 | 18.26 | 2.00 | <DL | 43.15 | 51.55 |
| DAT (48 hr) | 6.30 | 8.49 | 2.50 | <DL | 92.29 | 96.03 |
| DAT (72 hr) | 6.54 | 8.28 | 2.49 | <DL | 86.38 | 95.88 |
| MPD (0 hr) | 147.28 | 23.44 | 1.92 | <DL | 0.00 | 0 |
| MPD (24 hr) | 6.42 | 9.14 | 2.90 | <DL | 77.25 | 95.64 |
| OPD (0 hr) | 156.03 | 20.62 | 1.39 | <DL | <DL | 0 |
| OPD (24 hr) | 118.20 | 18.69 | 1.65 | <DL | 16.80 | 24.24 |
| OPD (48 hr) | 5.28 | 8.41 | 2.11 | <DL | 86.88 | 96.61 |
| OPD (72 hr) | 5.40 | 7.91 | 2.32 | 0.36 | 90.28 | 96.53 |
| PPD (0 hr) | 154.69 | 20.93 | 1.49 | 3.40 | 2.09 | 0 |
| PPD (24 hr) | 117.27 | 18.73 | <DL | 0.30 | 13.74 | 24.18 |
| PPD (48 hr) | 3.48 | 8.31 | 2.15 | 0.37 | 84.75 | 97.75 |
| PPD (72 hr) | 4.01 | 7.59 | 2.38 | <DL | 84.79 | 97.40 |
| Pure Glucose (0 hr) | 146.38 | <DL | <DL | <DL | <DL | 0 |
| Pure Glucose (24 hr) | <DL | <DL | <DL | <DL | 77.39 | 100 |
| Pure Glucose (48 hr) | <DL | <DL | 2.31 | <DL | 83.57 | 100 |

DL: detection limit growth nutrients, and these compositions were then inoculated with 5% inoculum of *Saccharomyces cerevisiae* (optical density 10). If more than 80% of sugars were consumed in 72 hours of fermentation, the test is considered a "pass" (i.e., a satisfactory test result). The results of the fermentation tests over time are set forth in Table 7.

TABLE 7

| Composition (time) | Glucose (g/l) | Xylose (g/l) | Acetic Acid (g/l) | HMF (g/l) | Ethanol (g/l) | % Glucose Consumed |
|---|---|---|---|---|---|---|
| Sugar Liquor (before contact with amine) | 178.30 | 24.71 | 1.53 | 8.78 | <DL | 0 |
| Piperidine (0 hr) | 156.87 | 21.63 | 1.55 | 6.13 | <DL | 0 |
| Piperidine (24 hr) | 148.05 | 20.48 | 1.36 | 5.51 | 2.71 | 5.62 |
| Piperidine (48 hr) | 147.80 | 20.51 | 1.49 | 5.61 | 2.15 | 5.78 |
| Piperidine (72 hr) | 148.41 | 20.54 | 1.54 | 5.31 | 2.37 | 5.39 |
| Piperidine (120 hr) | 144.24 | 19.97 | 1.47 | 4.83 | 2.49 | 8.05 |
| Diethanolamine (0 hr) | 156.98 | 21.72 | 1.56 | 7.04 | <DL | 0 |
| Diethanolamine (24 hr) | 148.17 | 20.92 | 2.20 | 6.16 | 2.51 | 5.61 |
| Diethanolamine (48 hr) | 146.86 | 20.37 | 1.38 | 5.80 | 2.15 | 6.44 |
| Diethanolamine (72 hr) | 146.53 | 20.31 | 1.50 | 5.56 | 2.35 | 6.65 |
| Diethanolamine (120 hr) | 143.29 | 19.85 | 1.45 | 5.55 | 2.25 | 8.72 |
| Ethanolamine (0 hr) | 155.94 | 21.37 | 1.50 | 6.01 | 0.92 | 0 |
| Ethanolamine (24 hr) | 143.58 | 19.87 | 1.49 | 5.24 | 3.53 | 7.92 |
| Ethanolamine (48 hr) | 146.12 | 20.23 | 1.52 | 5.03 | 2.74 | 6.29 |
| Ethanolamine (72 hr) | 144.31 | 20.07 | 1.47 | 4.67 | 2.92 | 7.45 |
| Ethanolamine (120 hr) | 136.08 | 19.20 | 2.38 | 4.46 | 3.54 | 12.73 |
| Melamine (0 hr) | 159.77 | 21.79 | 1.4 | 7.52 | <DL | 0 |
| Melamine (24 hr) | 152.99 | 21.01 | 1.39 | 6.59 | 2.13 | 4.24 |
| Melamine (48 hr) | 153.13 | 21.08 | 1.45 | 6.47 | 2.48 | 4.15 |
| Melamine (72 hr) | 151.83 | 21.01 | 1.34 | 6.45 | 2.1 | 4.97 |
| Urea (0 hr) | 159.33 | 22.10 | 1.56 | 7.44 | 1.38 | 0 |
| Urea (24 hr) | 149.48 | 20.85 | 1.40 | 6.58 | 2.72 | 6.18 |
| Urea (48 hr) | 152.17 | 21.13 | 1.45 | 6.49 | 2.23 | 4.49 |
| Urea (72 hr) | 149.21 | 20.70 | 1.41 | 6.06 | 2.39 | 6.35 |
| Urea (120 hr) | 145.80 | 20.22 | 1.47 | 5.66 | 2.41 | 8.49 |
| Aniline (0 hr) | 154 | 22 | 1.55 | 7.34 | 1.7 | 0 |
| Aniline (24 hr) | 146 | 21 | 1.35 | 5.2 | 1.55 | 5.19 |
| Aniline (48 hr) | 146 | 20 | 1.28 | 4.89 | 1.51 | 5.19 |
| Aniline (72 hr) | — | — | — | — | — | — |
| Pure Glucose (0 hr) | 145.38 | <DL | <DL | <DL | <DL | 0 |
| Pure Glucose (24 hr) | <DL | <DL | 0.95 | <DL | 70.70 | 100 |
| Pure Glucose (48 hr) | <DL | <DL | 1.25 | <DL | 69.57 | 100 |

DL: detection limit

As shown in Table 7, none of the samples that were contacted with an amine that is not a compound of formula (I) passed the fermentation test.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a saccharide-containing composition comprising contacting a composition containing a saccharide with a compound of formula (I) or a salt thereof

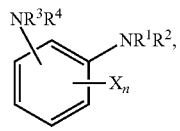

(I)

wherein
(1) $R^1$-$R^4$ are the same or different and each is independently: —H, -M, $C_1$-$C_8$ alkyl, alkylene oxide, oligoalkylene oxide, or polyalkylene oxide, or
any two of $R^1$-$R^4$ taken together is a divalent counterion, and the other two of $R^1$-$R^4$ is defined as in (1); or
any three of $R^1$-$R^4$ taken together is a trivalent counterion, and the other one of $R^1$-$R^4$ is defined as in (1); or
any two of $R^1$-$R^4$ taken together is a divalent counterion, and the other two of $R^1$-$R^4$ is the same or a different divalent counterion; or
all of $R^1$-$R^4$ taken together is a tetravalent counterion;
(2) each X is the same or different and each is independently: —H, —OH, $C_1$-$C_8$ alkyl, $C_2$-$C_8$ alkenyl, alkylene oxide, oligoalkylene oxide, polyalkylene oxide, halo, —$NO_2$, —$R^7NO_2$, —$OR^8$, —$R^7OR^8$, —$OR^7OR^8$, —OM, —$R^7OM$, —$CONH_2$, —$R^7CONH_2$, —$C(O)OR^8$, —$R^7C(O)OR^8$, —$C(O)OM$, —$R^7C(O)OM$, —$C(O)R^8$, —$R^7C(O)R^8$, —$PO_4$, —$R^7PO_4$, —$SO_3H$, —$SO_3M$, —$R^7SO_3H$, —$R^7SO_3M$, —$NR^8R^9$, —$R^7NR^8R^9$;
(3) $R^7$ is a divalent $C_1$-$C_8$ alkylene, alkylene oxide, oligoalkylene oxide, or polyalkylene oxide group, and $R^8$ and $R^9$ are the same or different and each is independently: —H, $C_1$-$C_8$ alkyl, alkylene oxide, oligoalkylene oxide, or polyalkylene oxide;
(4) M is a monovalent counterion;
(5) n is 0 or an integer of 1 to 4;
(6) the saccharide-containing composition comprises a hydrolysis product of a lignocellulosic feedstock; and
(7) the saccharide in the saccharide-containing composition comprises an oligosaccharide derived from a cellulose portion of the lignocellulosic feedstock.

2. The method of claim 1, wherein the saccharide is: a monosaccharide that is xylose, a monosaccharide that is glucose, an oligosaccharide comprising xylose, an oligosaccharide comprising glucose, a polysaccharide comprising xylose, or a polysaccharide comprising glucose, or any combination thereof.

3. The method of claim 1, wherein the composition further comprises an aldehyde.

4. The method of claim 3, wherein the aldehyde is: hydroxymethylfurfural (HMF), furfural, syringaldehyde, or acetaldehyde.

5. The method of claim 3, further comprising reducing the amount of aldehyde in the composition after contact with the compound of formula (I) as compared to the amount of aldehyde in the composition prior to contact with the compound of formula (I).

6. The method of claim 5, wherein the aldehyde concentration in the composition prior to contacting the composition with the compound of formula (I) is greater than about 1.5 g/L, and the aldehyde concentration in the composition is about 1.5 g/L or less after contacting the composition with the compound of formula (I).

7. The method of claim 1, wherein
each of $R^1$-$R^4$ is —H, or -M; or
two or more of $R^1$-$R^4$ are taken together to be a divalent counterion, a trivalent counterion, or a tetravalent counterion.

8. The method of claim 1, wherein n is 1 and X is not —H.

9. The method of claim 1, wherein X is $C_1$-$C_8$ alkyl, alkylene oxide, oligoalkylene oxide, polyalkylene oxide, —OM, —$OR^8$, —$R^7OR^8$, —$R^7OM$, —$C(O)OR^8$, —$C(O)R^8$, —$PO_4$, —$SO_3H$, —$SO_3M$, —$R^7SO_3H$, —$R^7SO_3M$, or —$NR^7R^8$.

10. The method of claim 1, wherein n is 0.

11. The method of claim 1, wherein the compound of formula (I) is: o-phenylenediamine, p-phenylenediamine, or 2,4-diaminotoluene, or a salt thereof, or any combination thereof.

12. The method of claim 1, wherein the compound of formula (I) is m-phenylenediamine or a salt thereof.

13. The method of claim 1, further comprising adjusting the pH of the composition to about 5-9 before contacting the composition with the compound of formula (I).

14. The method of claim 1, wherein the composition is not subjected to an overliming step.

15. The method of claim 1, further comprising transforming at least a portion of the composition by one or more of the following transformations: a catalytic treatment, a biocatalytic treatment, a non-catalytic treatment, or an enzymatic treatment, or a combination thereof before, during, or after contacting the composition with the compound of formula (I).

16. The method of claim 1, wherein the compound of formula (I) is incorporated onto, embedded in, complexed to, or electrostatically bound to a solid support or is grafted to a polymer.

17. A composition comprising a saccharide and a compound of formula (I) or a salt thereof

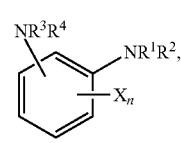

(I)

wherein
(1) $R^1$-$R^4$ are the same or different and each is independently: —H, -M, $C_1$-$C_8$ alkyl, alkylene oxide, oligoalkylene oxide, polyalkylene oxide; or
any two of $R^1$-$R^4$ taken together is a divalent counterion, and the other two of $R^1$-$R^4$ is defined as in (1); or
any three of $R^1$-$R^4$ taken together is a trivalent counterion, and the other one of $R^1$-$R^4$ is defined as in (1); or
any two of $R^1$-$R^4$ taken together is a divalent counterion, and the other two of $R^1$-$R^4$ is the same or a different divalent counterion; or
all of $R^1$-$R^4$ taken together is a tetravalent counterion;
(2) each X is the same or different and each is independently: —H, —OH, $C_1$-$C_8$ alkyl, $C_2$-$C_8$ alkenyl, alkylene oxide, oligoalkylene oxide, polyalkylene oxide, halo, —$NO_2$, —$R^7NO_2$, —$OR^8$, —$R^7OR^8$, —$OR^7OR^8$, —OM, —$R^7OM$, —$CONH_2$, —$R^7CONH_2$, —$C(O)OR^8$, —$R^7C(O)OR^8$, —$C(O)OM$, —$R^7C(O)OM$, —$C(O)R^8$, —$R^7C(O)R^8$, —$PO_4$, —$R^7PO_4$, —$SO_3H$, —$SO_3M$, —$R^7SO_3H$, —$R^7SO_3M$, —$NR^8R^9$, —$R^7NR^8R^9$;
(3) $R^7$ is a divalent $C_1$-$C_8$ alkylene, alkylene oxide, oligoalkylene oxide, or polyalkylene oxide group, and $R^8$ and $R^9$ are the same or different and each is independently: —H, $C_1$-$C_8$ alkyl, alkylene oxide, oligoalkylene oxide, or polyalkylene oxide;
(4) M is a monovalent counterion;
(5) n is 0 or an integer of 1 to 4; and
(6) the saccharide-containing composition comprises a hydrolysis product of a lignocellulosic feedstock; and
(7) the saccharide in the saccharide-containing composition comprises an oligosaccharide derived from a cellulose portion of the lignocellulosic feedstock.

18. The composition of claim 17, wherein the saccharide is: a monosaccharide that is xylose, a monosaccharide that is glucose, an oligosaccharide comprising xylose, an oligosaccharide comprising glucose, a polysaccharide comprising xylose, or a polysaccharide comprising glucose, or any combination thereof.

19. The composition of claim 17, wherein
each of $R^1$-$R^4$ is —H, or -M; or
two or more of $R^1$-$R^4$ are taken together to be a divalent counterion, a trivalent counterion, or a tetravalent counterion.

20. The composition of claim 17, wherein n is 1 and X is not —H.

21. The composition of claim 17, wherein X is $C_1$-$C_8$ alkyl, alkylene oxide, oligoalkylene oxide, polyalkylene oxide, —OM, —$OR^8$, —$R^7OR^8$, —$R^7OM$, —$C(O)OR^8$, —$C(O)R^8$, —$PO_4$, —$SO_3H$, —$SO_3M$, —$R^7SO_3H$, —$R^7SO_3M$, or —$NR^7R^8$.

22. The composition of claim 17, wherein n is 0.

23. The composition of claim 17, wherein the compound of formula (I) is: o-phenylenediamine, p-phenylenediamine, or 2,4-diaminotoluene, or a salt thereof, or any combination thereof.

24. The composition of claim 17, wherein the compound of formula (I) is m-phenylenediamine or a salt thereof.

25. The composition of claim 17, further comprising an aldehyde in an amount of about 1.5 g/L or less.

26. The composition of claim 25, wherein the aldehyde is: hydroxymethylfurfural (HMF), furfural, syringaldehyde, or acetaldehyde.

* * * * *